(12) United States Patent
Heesch

(10) Patent No.: US 6,645,160 B1
(45) Date of Patent: Nov. 11, 2003

(54) GUIDE SUPPORT CATHETER

(76) Inventor: Christian M. Heesch, #1 Stones Throw Dr., Houma, LA (US) 70364

( * ) Notice: Subject to any disclaimer, the term of this patent is extended or adjusted under 35 U.S.C. 154(b) by 90 days.

(21) Appl. No.: 09/587,630

(22) Filed: Jun. 5, 2000

Related U.S. Application Data

(60) Provisional application No. 60/190,263, filed on Mar. 17, 2000.

(51) Int. Cl.[7] .................................................. A61B 5/00
(52) U.S. Cl. .................. 600/585; 128/207.14; 604/523
(58) Field of Search ................... 604/104–107, 604/95.04, 528, 523, 532; 600/585; 128/207.14

(56) References Cited

U.S. PATENT DOCUMENTS

| | | | | |
|---|---|---|---|---|
| 4,674,495 A | * | 6/1987 | Orr ........................ 128/207.14 |
| 4,748,982 A | | 6/1988 | Horzewski et al. ......... 604/102 |
| 4,781,682 A | | 11/1988 | Patel ........................... 604/96 |
| 4,813,930 A | * | 3/1989 | Elliott ........................ 600/585 |
| 5,061,273 A | | 10/1991 | Yock |
| 5,098,412 A | * | 3/1992 | Shiu ........................... 600/585 |
| 5,263,963 A | * | 11/1993 | Garrison et al. ............. 604/104 |
| 5,306,261 A | | 4/1994 | Alliger et al. |
| 5,336,184 A | | 8/1994 | Teirstein ..................... 604/102 |
| 5,365,943 A | * | 11/1994 | Jansen ........................ 600/585 |
| 5,443,456 A | | 8/1995 | Alliger et al. |
| 5,456,667 A | * | 10/1995 | Ham et al. ................... 604/107 |
| 5,681,280 A | * | 10/1997 | Rusk et al. .................. 604/105 |
| 5,776,096 A | | 7/1998 | Fields ......................... 604/43 |
| 5,820,592 A | | 10/1998 | Hammerslag ............... 604/95 |
| 5,885,259 A | * | 3/1999 | Berg ........................... 604/523 |
| 5,941,872 A | * | 8/1999 | Berg ........................... 604/532 |
| 5,984,878 A | * | 11/1999 | Engelson .................... 600/585 |
| 6,083,213 A | * | 7/2000 | Voda ........................... 604/523 |
| 6,350,252 B2 | * | 2/2002 | Ray et al. ................... 604/107 |

* cited by examiner

*Primary Examiner*—Thomas Denion
*Assistant Examiner*—Thai-Ba Trieu
(74) *Attorney, Agent, or Firm*—Garvey, Smith, Nehrbass & Doody, L.L.C.; Charles C. Garvey, Jr.; Seth M. Nehrbass

(57) ABSTRACT

The invention provides a catheter, to be used preferably for cardiac diagnostic and interventional procedures, comprising an elongated tubular body having a proximal and a distal end, and at least one lumen extending axially therethrough. A plurality of support members (e.g. wires) extends through the catheter, essentially parallel to its axis, exits the catheter at a defined distance from its distal opening, and is attached at the catheter in proximity to its distal end. Manipulation of these support members leads to their flexing outward or their retraction towards the catheter, providing an adjustable support for the catheter enabling a safer and more secure engagement of the ostia of coronary arteries.

85 Claims, 6 Drawing Sheets

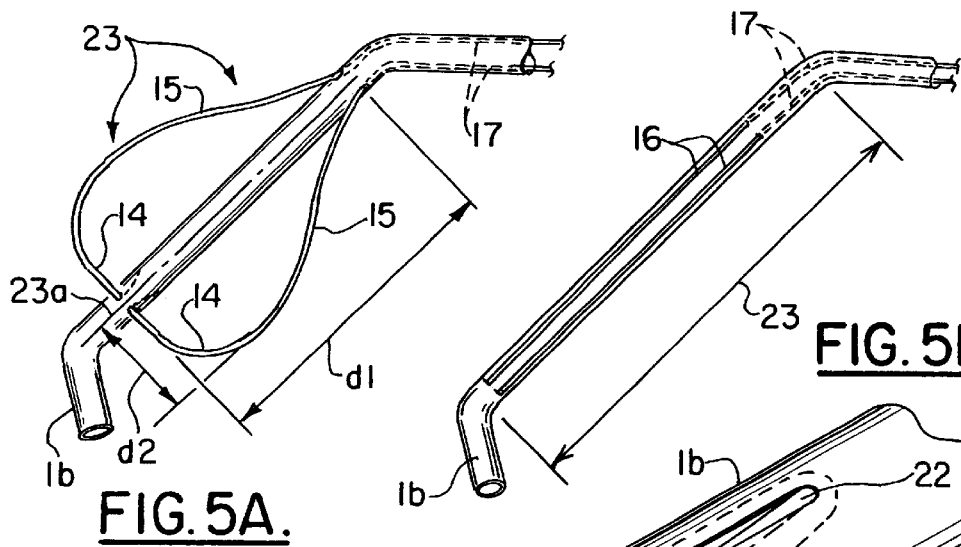
FIG. 5A.
FIG. 5B.
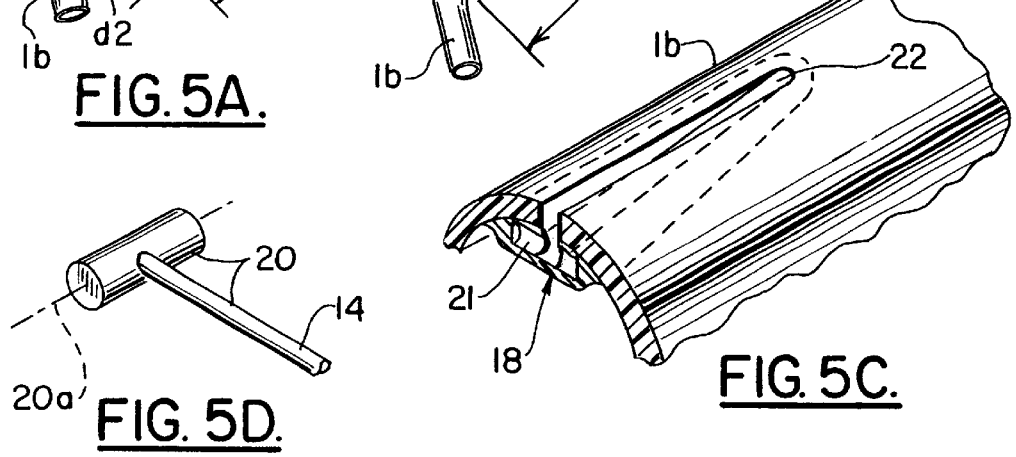
FIG. 5C.
FIG. 5D.
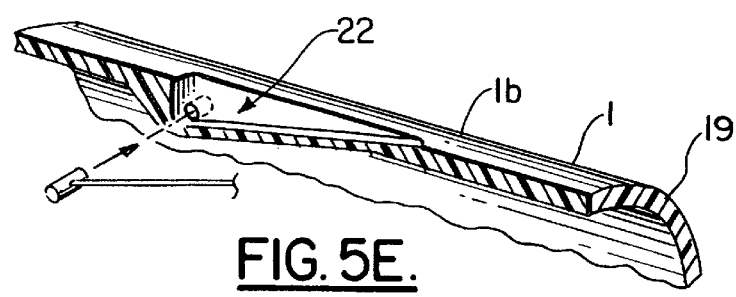
FIG. 5E.
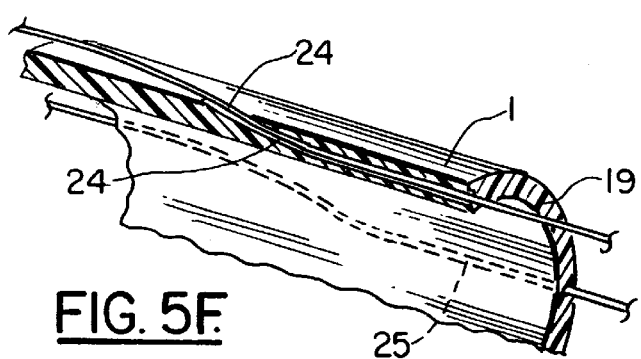
FIG. 5F.

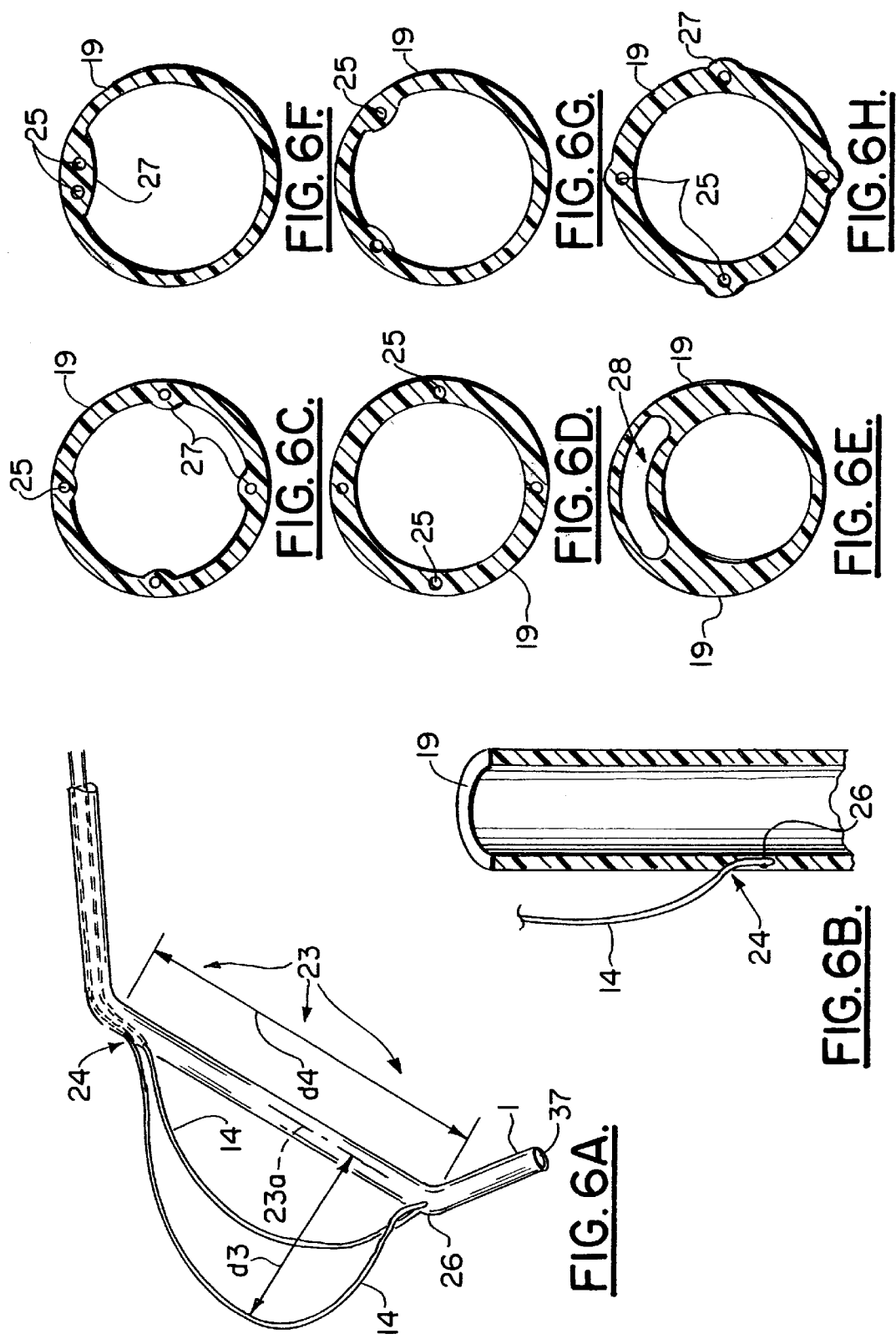

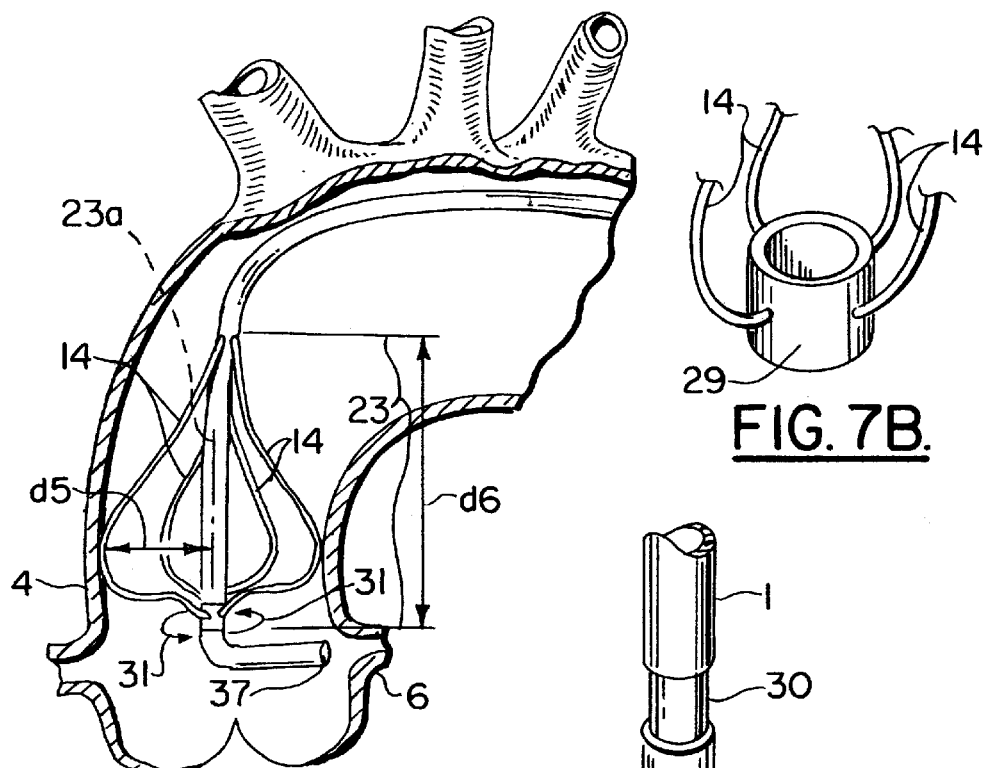
FIG. 7A.
FIG. 7B.
FIG. 7C.
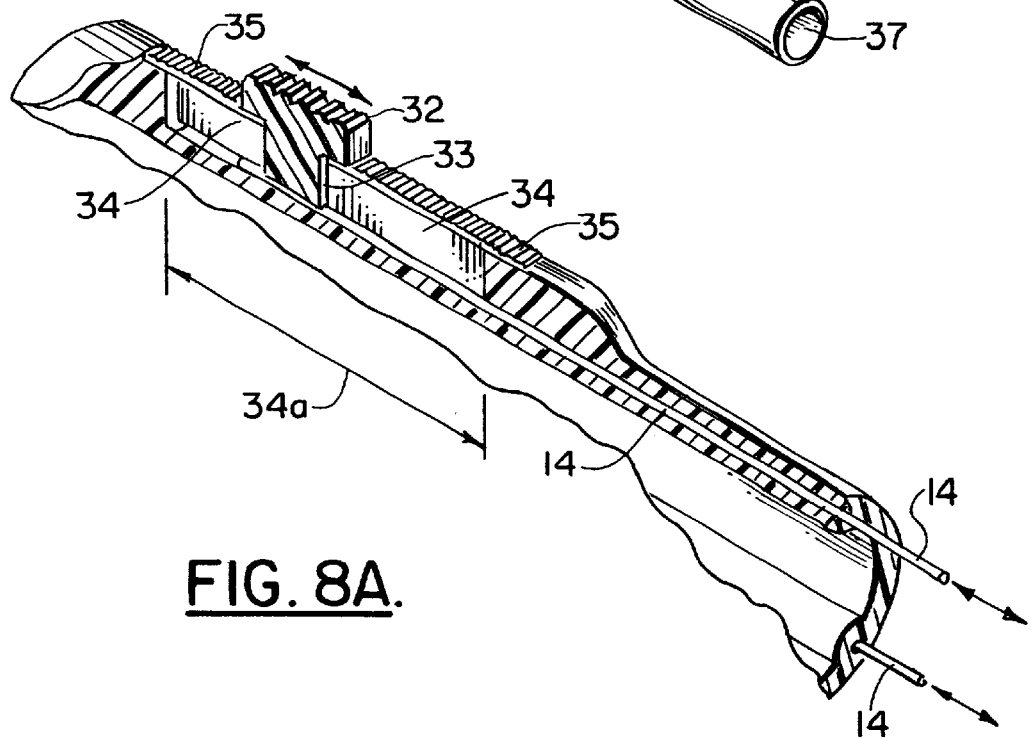
FIG. 8A.

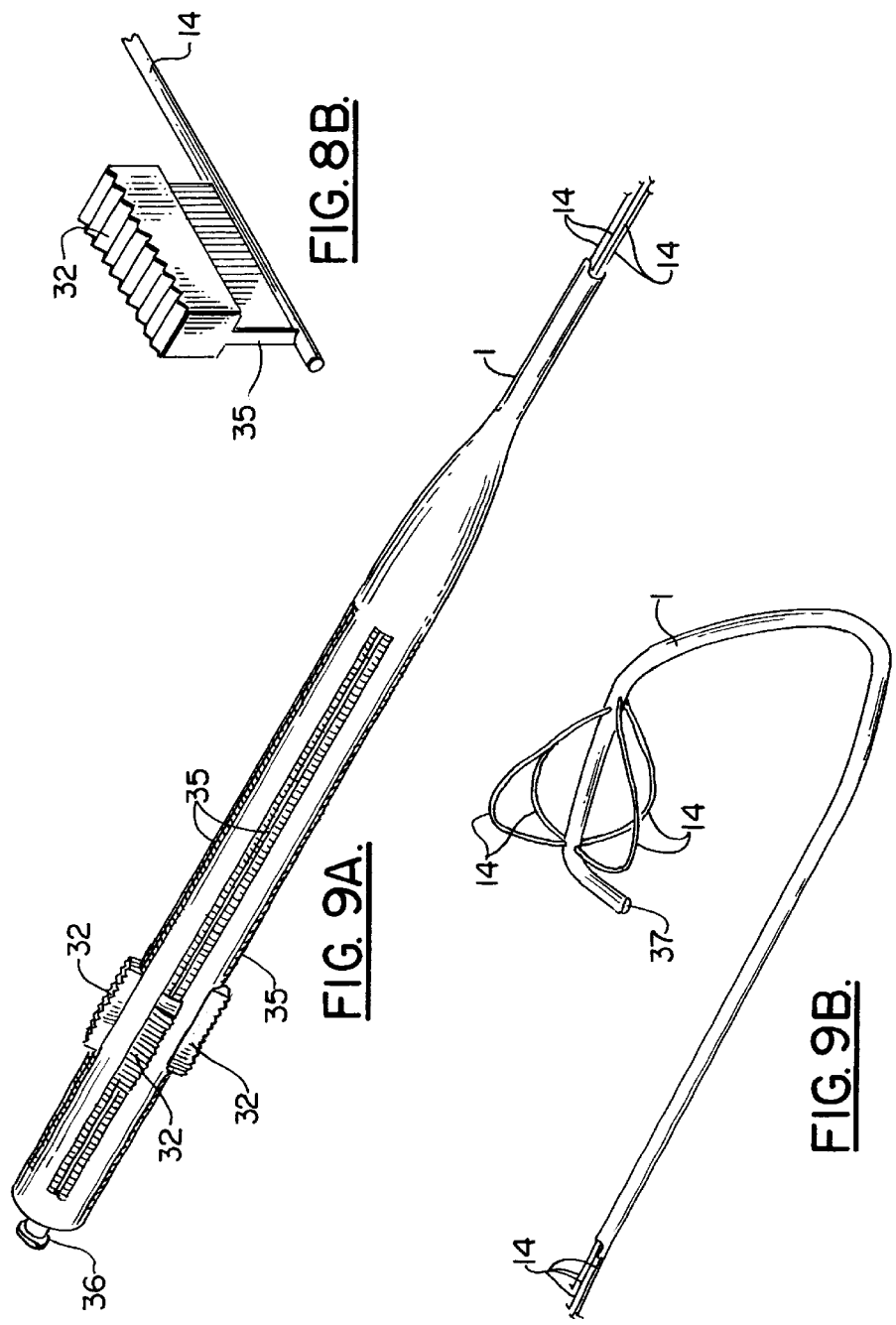

GUIDE SUPPORT CATHETER

CROSS-REFERENCE TO RELATED APPLICATIONS

Priority of U.S. Provisional Patent Application Serial No. 60/190,263, filed Mar. 17, 2000, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The apparatus of the present invention relates to angiographic catheters or guide catheters for coronary angioplasty or other coronary or vascular intervention.

2. General Background of the Invention

During percutaneous coronary intervention, guide catheters are advanced from the periphery, usually the femoral artery, into the aorta. The tip of the catheter is positioned in the ostium of a coronary artery. Subsequently, wires, balloon catheters, and other equipment are advanced through the guide catheter into the large epicardial coronary arteries to treat stenotic lesions.

A common problem during these procedures is the lack of guide support. As the operator attempts to advance the interventional equipment into the correct position within the coronary circulation, mechanical resistance is frequently encountered. This mechanical resistance may be due to a variety of factors, including but not confined to tortuosity of the target vessel, tight narrowing or calcification of stenoses, or lack of flexibility of the equipment used. This resistance may often have to be overcome by applying increased mechanical push of the equipment. Many guide catheters, however, lack sufficient stiffness to allow this somewhat forceful passing of the interventional equipment, and back out of their ostial position.

Operators will typically attempt to tackle this problem through changes of their interventional equipment such as wires or balloons, or through the exchange of their guide catheter for a stiffer or differently shaped model. Prolongation of the procedure with increased radiation exposure to the patient and operators, wasting of interventional equipment, and the abandoning of the type of intervention best suited for an individual lesion in favor of a suboptimal method requiring less guide support are all frequently seen consequences of lack of guide support. Moreover, the repeated, often forceful engagement of a coronary ostium with ill fitted equipment frequently leads to endothelial trauma and at times even to the dissection of the coronary artery.

BRIEF SUMMARY OF THE INVENTION

The suggested new guide catheter features a plurality of wires, which are contained within the lumen of the catheter, extending from the proximal end of the catheter until its tip. Exit openings lead the wires outside the catheter lumen for a defined distance. Near the distal end of the catheter, the wires re-enter the catheter, and are securely anchored at or within the catheter wall.

A second segment of exposure of the wires to the exterior of the catheter is located at its proximal portion, the catheter segment which is not inserted into the patient's vascular system, and which is manipulated by the operator. Small knobs on the outside of the catheter are connected to the wires at the proximal segment of the catheter. These small knobs connected to the wires allow the operator to advance and retract them, leading to their flexing away from (with advancing movements of the wires) or their repositioning adjacent to the body of the catheter (with retracting movements of the wires) at a defined section near its distal end. The bending out of the wire forms supporting loops, which firmly anchor the distal portion within the aortic root. The knobs located at the proximal portion of the wires allow for their being locked in any position. Adjustment of the degree of extension or retraction of the wires, and thus the size of the distal wire loops, allows for a safe and secure engagement of the distal opening of the catheter within the coronary ostium targeted.

There are numerous advantages of the present invention, as listed below.

1. There is ample guide support for the pushing of interventional equipment into the coronary circulation, since the guide catheter is backed by its wires against the opposite wall of the aortic root.

2. The touching of the wire bends against the aortic root can be used by the operator to better steer the distal opening of the guide catheter through rotational movements.

3. Undue engagement of the coronary ostium can be avoided, significantly lessening the risk of proximal ostial trauma of the coronary artery by the catheter tip with possible injury to the ostial endothelium.

4. During coronary angioplasty, the ensemble of the wire bends, in fact, allows to reliably disengage the catheter tip from the coronary ostium throughout most of the procedure, providing adequate blood supply into the coronary without the fear of loss of catheter position.

5. The risk of loss of coronary wire position, a not infrequent and potentially disastrous event during angioplasty, is substantially lessened due to the secured guide catheter position.

6. Less deep engagement and better coronary flow avoid the need for guide catheters with side holes and their inherent disadvantages.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIG. 5A is a schematic view of parts of another embodiment of the present invention;

FIGS. 5B–5E are perspective, magnified views of parts of an embodiment of the present invention;

FIGS. 6A–6H are perspective, magnified views of the distal portion of one embodiment of the present invention;

FIGS. 7A–7C are views of one embodiment of the present invention;

FIGS. 8A and 8B are perspective, magnified views of the proximal element of the present invention; and FIGS. 9A and 9B are side views of the proximal and the distal end of the present invention.

DETAILED DESCRIPTION OF THE INVENTION

Figure 1:
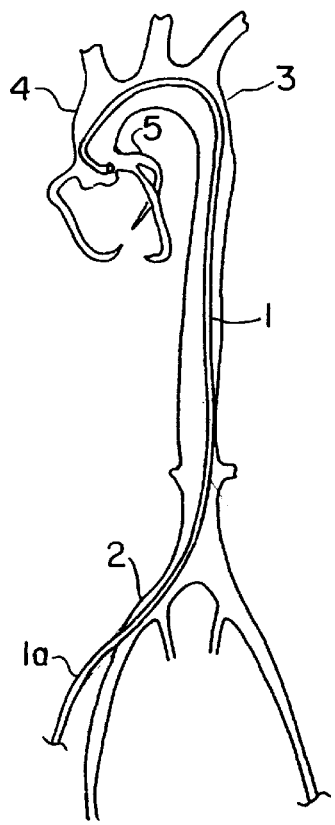
FIG. 1 is a schematic view of a typical catheter in the human aorta. Also shown are the coronary vessels and the major branches of the aorta.
Figure 2:
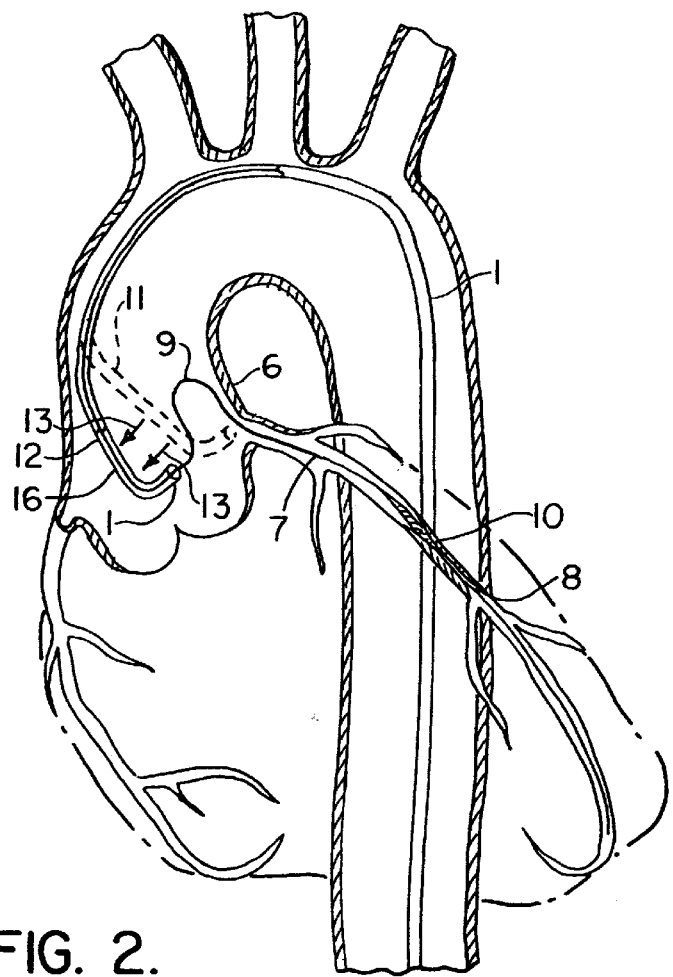
FIG. 2 is a schematic view of the aortic arch, the coronary vessels, a catheter, and a balloon catheter and wire assembly, illustrating the problem to be resolved with the present invention.

Referring now to the enclosed drawings, FIGS. 1 and 2 are intended to illustrate the setting in which the present invention is to be used.

FIG. 1 shows a schematic overview of anatomical landmarks and technical equipment used in a typical cardiac catheterization procedure. The catheter 1 enters the vascular system at the common femoral artery 2, follows the course of the aorta 3, and has been advanced with its distal end 1b or tip extending into the aortic root 4, just above the heart. The distal opening of the catheter engages a coronary artery 5. Through this catheter 1 or guide catheter, contrast dye is injected, and/or angioplasty equipment is advanced into the coronary system. The epicardial coronary arteries 5, but not the underlying heart muscle, have been depicted for clarity.

Catheter 1 thus provides a single tube or principal tube for conveying a selected fluid (e.g., dye) or a selected device (e.g., angioplasty equipment).

FIG. 2 illustrates the problem leading to the design of the present invention. The guide catheter 1 was engaged in the coronary ostium 6. A thin, flexible angioplasty wire 7 has crossed successfully a stenotic lesion or blockage 8. The operator now attempts to advance a balloon catheter 9 through the guide catheter 1 and over the wire 7 into the coronary system. However, the angioplasty balloon 10, and the balloon catheter 9 on which it is mounted, are unable to cross the blockage 8. Although the operator attempts to push the balloon 10 and the balloon catheter 9 through the blockage, the blockage 8 proves to be too recalcitrant. Thus, instead of crossing the blockage, the pushing of the balloon catheter 9 provides backward thrust and disengages the guide catheter 1 from its engaged position 11 within the coronary ostium 6 to an unstable, disengaged position 12, following the direction indicated by arrows 13, with subsequent buckling of the balloon catheter 9 and wire 7 assembly, leading to possible complete disengagement and loss of position of the entire equipment.

Figure 3:
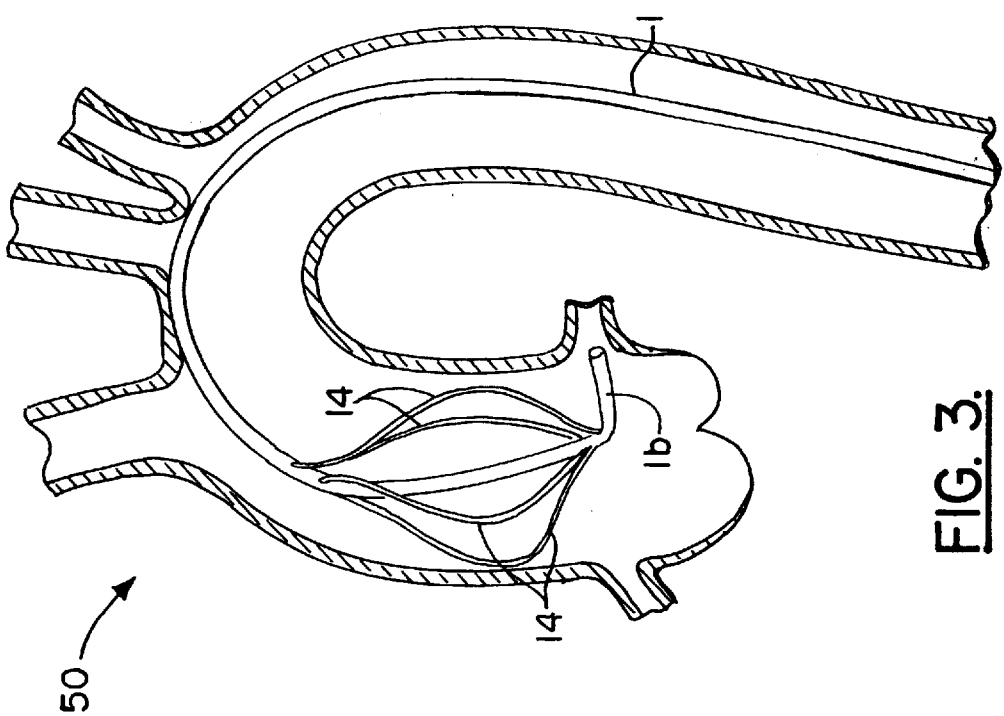
FIG. 3 is a schematic view of parts of the present invention and its method of use in the aortic arch.

FIG. 3 shows the new catheter of the present invention designated generally by the numeral 50 in FIG. 3. Catheter apparatus 50 includes a catheter body 1 that carries a plurality of thin, coated support wires 14. Wires 14 are movable (as selected by an operator, cardiologist, technician, or operating room nurse) between collapsed and extended positions. In FIG. 3, wires 14 are shown in the extended position, having exited the guide catheter body 1 and form bends around its distal end 1b portion. The guide catheter is now securely positioned within the aortic root 4, allowing the operator to firmly advance any equipment through the guide catheter 1 into the coronary system, without the risk of loss of guide catheter support. A remote actuator that can be manually, grasped by a user at the distal end portion of the body can be provided for moving the support wires 14 between collapsed and extended positions.

Extension of the support wires 14 on the side opposite to the coronary ostium 6 engaged will provide enhanced guide support. Extension of the support wires 14 on the ipsilateral side of the coronary ostium will prevent unduly deep engagement with possible endothelial ostial injury. Complete retraction of the wires 14 to the collapsed position would lead to their firm attachment to the catheter body 1 and the supportive loops would disappear (see FIG. 6b).

Figure 4:
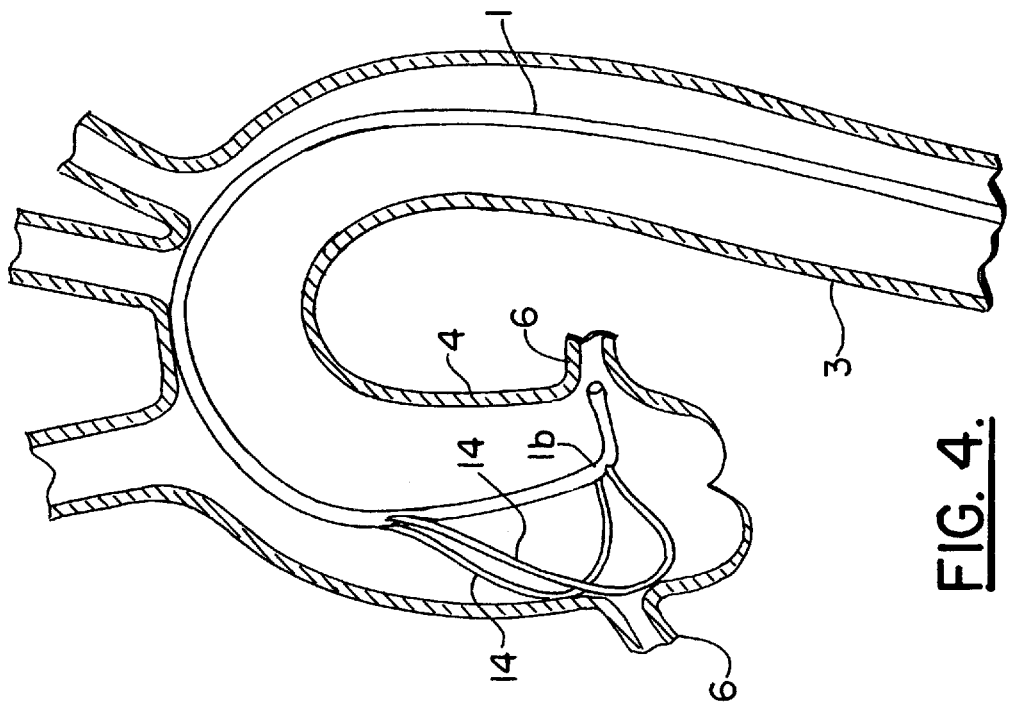
FIG. 4 is a schematic view of parts of another embodiment of the present invention and its method of use in the aortic arch.

FIG. 4 shows a similar schematic view, using two support wires 14 only. This embodiment of the catheter, although simpler than the previous one, will nonetheless reliably prevent loss of guide support. While it cannot prevent undue deep engagement of the coronary ostium through extension of support wires 14 on the ipsilateral side of the ostium engaged, it can lessen the likelihood of this problem through retraction of the contralateral support wires 14 in conjunction with appropriate catheter pre-shaping and inherent bias specifications (moving the tip of the catheter away from the ostium).

FIGS. 5A–5F show in more detail the support wires section 23 of catheter body 1, and the connection of each support wire 14 to the catheter 1 at the distal end 1B or tip of the catheter 1. FIG. 5a illustrates the wires 14, having exited the catheter body 1, and forming supportive bends or loops in an extended position 15. FIG. 5B shows the same wires 14, now in a retracted position 16. The path of the wires 14 within the catheter body 1 is indicated by dotted lines 17 in FIGS. 5A and 5B.

FIG. 5C shows in a partial perspective view, how the distal end of these wires 14 could be connected to small anchor bases 18 or receptacles within the catheter wall 19. The wires 14 have small, transversely positioned or orthogonal end pieces 20 at their tip, as shown in FIG. 5D. These orthogonal end pieces 20 rest in small axle joint sockets 21, a connection which allows for rotational or pivotal movements around the central longitudinal axis 20a of the orthogonal end pieces 20. Small longitudinal slits 22 receive the wires 14 from the outside at the distal end 1a of the support section 23 of catheter 1, and into the anchor bases 18. FIGS. 5E and 5F show lateral partial perspective views of this ensemble, which allows the wires 14 at the site of their distal attachment a high degree of freedom through pivotal movements.

FIG. 5F shows how the wires 14, at the proximal end of the support section 23, exit through small exit holes 24 from the catheter wall 19, within which they run through longitudinal wire channels or tracks 25. It is readily apparent that this path of the support wires 14, leaving through preformed, diagonal exit holes 24 at the proximal end of the support section 23, and re-attaching to the catheter at the distal end of the support section 23 into axle joint sockets 21 allowing for rotational freedom of the orthogonal end pieces 20, will lead to an essentially pear-shaped configuration of the support wires in their extended position 15, as illustrated in FIG. 5A. Further, the distance d2 that the extended wire is extended between exit hole 24 and anchor base 18 is preferably greater than the radial distance d1 between the central axis 23a of the support section and the extended position of wire 16.

FIGS. 6a and 6b show an alternate, somewhat simpler mode of attachment of the wires 14 at the distal end of the support section 23. As illustrated in FIG. 6b, the wires 14 are simply anchored within the catheter wall 19 at anchor point 26. If the inherent stiffness and bias of the wires 14 remains the same throughout the entire support section 23, and if the angle of the exit holes 24 is the same at the proximal and the distal ends of the support section 23, the wires 14, in any of their extended positions 15, will assume a shape similar to a Gaussian curve, as illustrated in FIG. 6a. However, simple variations between the angle of the exit holes 24, or in the inherent wire stiffness along the support section 23, could bias the wires in their extended positions 15 to assume an infinite variety of other pre-defined shapes, as best suited for the purpose of an individual catheter.

As with the embodiment of FIGS. 5a–5f, the wire 14 extends a distance d4 along catheter support section 23 that is greater than the radial distance d3 that wire 16 extends away from the central axis 23a of support section 23.

FIGS. 6C–6H show cross sectional views of various arrangements of the position of the wire tracks 25 within the catheter wall 19. The wire tracks 25 could be positioned in reinforced, thickened portions 27 of the catheter wall 19. Variations of the number of wire tracks 25, the shape of the thickened portions 27, and the positioning of the wire tracks 25 are shown. Lastly, a plurality of wires could be run through a designated wire lumen 28 with a proximal and a distal opening (not shown), that could be connected through a side port (not shown), allowing for it to be flushed and aspirated.

FIGS. 7A–7C show yet another embodiment of the present invention. Wires 14, at the distal end of the support section 23 occupied by wires 14, attach to a small ring 29, using either of the two attachment arrangements illustrated in FIGS. 5 and 6. Ring 29 fits into circular indentation 30, with rotational freedom of ring 29 with respect to catheter 1. The advantages of this arrangement are easily seen in FIG. 7A. The catheter 1 is securely positioned by wires 14 within the aortic root 4, preparing to engage the ostium 6 of the left main coronary artery. Torquing movements of the catheter 1 at its proximal end by the operator are now reliably transmitted into the distal opening of 37 the catheter 1 (arrows 31), without fear of laceration of the ostium 6 through jerking and unpredictable catheter movements. Once the optimal rotation of the distal catheter tip has been confirmed fluoroscopically, the catheter 1 can be safely engaged into the coronary ostium through manipulations of the wires 14. As with the embodiments of FIGS. 5A–5F and 6A–6B, each wire 14 preferably extends a distance d6 along support section 23 that is greater than the distance d5 that each wire 14 extends away from the central axis 23a of support section 23.

FIGS. 8a and 8b illustrate the proximal ends of wires 14 and the connections of wires 14 to small knobs 32 via small connection pieces 33. Knobs 32 move parallel to the catheter axis in longitudinal openings 34. Accordingly, the ensemble of wire 14, connection piece 33 and knob 32 moves slidably backward and forward. The range of motion is defined by the length 34a of the longitudinal openings 34. Any conventional connection (e.g. the cammed or transversely serrated surface 35 shown in FIG. 8a) between the bottom portion of the knobs 32 and the exterior surface of the catheter body 1 can be used to ensure that no longitudinal movements of the wires occur without intentional change of the knob 32 position by the operator.

FIGS. 9a and 9b are side views of the proximal and the distal ends of the present invention, showing the catheter with four support wires, its proximal 36 and its distal 37 openings.

Multiple variations of this catheter design could be proposed, including but not confined to running the wires inside or outside the catheter lumen. The wires could also run in a spiral configuration rather than straight, or their advancement could be obtained through a twisting mechanism or any other conventional mechanism, rather than the knobs suggested in the preceding illustrations.

The unique new feature of this invention is the fact that guide support problems are overcome through a plurality of coated wires exiting the catheter in proximity to its tip, forming loops of variable sizes, and allowing its secure positioning and the manipulation of angioplasty equipment through the guide catheter without the fear of loss of guide position. An embodiment of this present invention with a single support wire is also proposed.

It is important that the wires, at the support section (and thus at their site of exposure to the central circulation), be covered with a special coating preventing the adhesion and aggregation of platelets with subsequent clot formation. Special lubrication (e.g. hydrophilic surface material) of the wire tracks with special fluid suitable to enhance the slidability of the wires and to prevent clot formation would be advisable.

The illustrations of this new invention show a Judkins Left catheter, however, multiple other commonly used catheter shapes would also be suitable for this invention, including but not confined to the Judkins Right, the Amplatz, and the Multipurpose catheters. While the advantages of the above described catheter were shown for a guide catheter for coronary intervention, minor modifications of this new catheter design could also be used for other vascular diagnostic or interventional catheters (e.g. for the safe engagement of coronary arteries or bypass grafts with tight ostial stenoses) renal artery catheters, carotid catheters, and other vascular and non-vascular medical catheters.

| PARTS | |
|---|---|
| PART NUMBER | DESCRIPTION |
| 1 | catheter |
| 1a | proximal end |
| 1b | distal end |
| 2 | common femoral artery |
| 3 | aorta |
| 4 | aortic root |
| 5 | coronary artery |
| 6 | coronary ostium |
| 7 | angioplasty wire |
| 8 | blockage |
| 9 | balloon catheter |
| 10 | balloon |
| 11 | engaged position |
| 12 | disengaged position |
| 13 | arrows |
| 14 | support wires |
| 15 | extended wire position |
| 16 | retracted wire position |
| 17 | wire path |
| 18 | internal anchor base |
| 19 | catheter wall |
| 20 | orthogonal end piece |
| 20a | central axis |
| 21 | axle joint sockets |
| 22 | longitudinal slits |
| 23 | support wires section |
| 23a | central longitudinal axis |
| 24 | exit holes |
| 25 | wire tracks |
| 26 | anchor point |
| 27 | thickened wall portion |
| 28 | designated wire lumen |
| 29 | ring |
| 30 | circular indentation |
| 31 | arrows |

-continued

PARTS

| PART NUMBER | DESCRIPTION |
|---|---|
| 32 | knobs |
| 33 | connection pieces |
| 34 | longitudinal openings |
| 34a | distance arrow |
| 35 | cammed surface |
| 36 | proximal opening |
| 37 | distal opening |
| 50 | catheter apparatus |
| d1 | distance arrow |
| d2 | distance arrow |
| d3 | distance arrow |
| d4 | distance arrow |
| d5 | distance arrow |
| d6 | distance arrow |

The foregoing embodiments are presented by way of example only; the scope of the present invention is to be limited only by the following claims.

What is claimed is:

1. A vascular catheter comprising:
   a) a catheter body having a proximal end, a distal end, at least one inner lumen, and an outer surface;
   b) a plurality of flexible support members attached to said outer surface of said catheter body at the distal end thereof, said support members being movable between a resting configuration positioned adjacent and generally parallel to said outer surface, and a support configuration wherein they are smoothly curved and extending away from said outer surface.

2. The vascular catheter of claim 1 wherein said one or more support members run slidably from the distal attachment at said catheter body to the proximal end of said catheter body, whereby movements of said support members towards the distal end of said catheter body lead to the flexing away of support means from a defined section near the distal end of said catheter (hereafter referred to as support section), and movements of said support means towards the proximal end of said catheter lead to the positioning adjacent to said catheter.

3. The catheter as in claim 2 wherein said one or more flexible support members are comprised of wires.

4. The catheter as in claim 3 wherein said one or more wires run from the distal support section towards the proximal end of the catheter body through elongated tubular openings within the catheter wall.

5. The catheter as in claim 3 wherein said one or more wires end near the tip of the catheter.

6. The catheter as in claim 3, wherein said one or more wires run from the distal support section towards the proximal end of the catheter inside a lumen of the catheter.

7. The catheter as in claim 3, wherein a selected one of said wires assumes a variety of intermediate positions between the resting position and the extended position.

8. The catheter as in claim 3, wherein a plurality of said wires assumes a variety of intermediate positions between the resting position and the fully extended support position.

9. The catheter as in claim 8, wherein each of said wires is linked to a knob at the outer surface at the proximal end of said catheter, said wires being linked to said knobs by means of small connection pieces slidably positioned in longitudinal slots of a catheter wall.

10. The catheter as in claim 9, wherein the intersection between the outer surface of said catheter wall and the lower surface of said knobs is a cammed surface connection, said connection allowing to securely position said knobs at any intermediate position along the full length of said slots of said catheter wall.

11. The catheter as in claim 3, wherein the wires are firmly attached at the distal end near the tip of the catheter.

12. The catheter of claim 11 wherein the wires used are attached to a ring at the distal end, said ring enclosing the circumference of the catheter near the distal end, the connection between said ring and said catheter allowing for rotation, but not for coaxial movements of the catheter.

13. The catheter of claim 12, wherein the connection between said ring and said catheter enables both rotational and coaxial movements.

14. The catheter as in claim 3, wherein the wires are movably attached at the distal end by means of pivoting joints.

15. The catheter as in claim 3, wherein the inherent flexibility of the wires differs from said support section and the section between said support section and said knobs.

16. The catheter as in claim 3, wherein the inherent flexibility of the wires remains the same throughout the entire length from said support section to said knobs.

17. The catheter as in claim 3, wherein the inherent flexibility of the wires changes along the length of the support section.

18. The catheter of claim 3, wherein the inherent flexibility of the wires remains unchanged along the support section.

19. The catheter of claim 3, wherein all wires are of the same length.

20. The catheter of claim 3, wherein the wires used have different lengths.

21. The catheter of claim 3, wherein the wires used have different lengths, and more than one support sections are formed.

22. The catheter as in claim 3, wherein said one or more wires are movably attached at the distal end by means of pivoting joints.

23. The catheter as in claim 3, wherein the inherent flexibility of said one or more wires changes along the length of said wires.

24. The catheter as in claim 3, wherein said one or more wires used are attached to a ring at the distal end, said ring enclosing the circumference of the catheter near the distal end, the connection between said ring and said catheter allowing for rotation, but not for coaxial movements of the catheter.

25. The catheter as in claim 3, wherein said one or more wires used are attached to a ring at the distal end, said ring enclosing the circumference of the catheter near its distal end, the connection between said ring and said catheter allowing both rotational and coaxial movements.

26. The catheter as in claim 3, wherein said one or more wires have means to be moved separately between the support configuration and the resting configuration.

27. The catheter as in claim 26, wherein each of said one or more wires is linked to a knob at the outer surface at the proximal end of said catheter, said wires being linked to said knobs by means of small connection pieces slidably positioned in longitudinal slots of a catheter wall.

28. The catheter as in claim 27, wherein the intersection between the outer surface of said catheter wall and the lower surface of said knobs is a cammed surface connection, said connection allowing to securely position said knobs at any intermediate position along the full length of said slots of said catheter wall.

29. The catheter apparatus of claim 2, whereby the support members are covered with a hydrophilic surface material, preventing platelet adhesion and aggregation.

30. A vascular catheter comprising:
 a) a catheter body having a proximal end, a distal end, at least one inner lumen, and an outer surface;
 b) one or more flexible support members attached to said outer surface of said catheter body at the distal end thereof, said support members being movable between a resting configuration positioned adjacent and generally parallel to said outer surface, and a support configuration wherein they are smoothly curved and extending away from said outer surface of said catheter;
 c) wherein a plurality of support members are used, each of said support members is moved separately between the support configuration and the resting configuration.

31. The catheter of claim 30 wherein the support members are covered with a hydrophilic surface material, preventing platelet adhesion and aggregation.

32. A cardiac catheter apparatus comprising:
 a) a catheter body having proximal and distal end portions and a central lumen with a central longitudinal axis;
 b) the distal end portion of the body having a tip that extends laterally away from the central longitudinal axis of the lumen at the distal end portion of the catheter body;
 c) a support, comprised of a plurality of individual support members that extends radially from the catheter body to engage an aortic root, said support including a smoothly curved surface that gently engages the tissue of the aortic root during use;
 d) wherein the support is movable between extended and retracted positions; and
 e) a remote actuator that is manually grasped by a user at the distal end portion of the body for moving the support between extended and collapsed positions.

33. The catheter apparatus of claim 32 wherein the catheter body has a wall and the support is slidably mounted in the wall at least along a portion of the length of the catheter wall.

34. The catheter apparatus of claim 32 wherein the support member tracks a generally pear shaped smooth curved shape when in the extended position.

35. The catheter apparatus of claim 32 wherein the tip forms an obtuse angle with the remainder of the catheter body.

36. The catheter apparatus of claim 35 wherein the support extends longitudinally in a proximal direction from the tip.

37. The catheter of claim 32 wherein the support members are covered with a hydrophilic surface material, preventing platelet adhesion and aggregation.

38. A cardiac catheter apparatus comprising:
 a) a catheter body having proximal and distal end portions and a central lumen with a central longitudinal axis;
 b) the distal end portion of the body having a tip that extends laterally away from the central longitudinal axis of the lumen at the distal end portion of the catheter body;
 c) a support that extends radially from the catheter body to engage an aortic root, said support including a smoothly curved surface that gently engage the tissue of the aortic root during use;
 d) wherein the support is movable between extended and retracted positions;
 e) a remote actuator that is manually grasped by a user at the distal end portion of the body for moving the support between extended and retracted positions; and
 f) wherein the support is comprised of a plurality of individual wire members.

39. The catheter of claim 38 wherein the support members are covered with a hydrophilic surface material, preventing platelet adhesion and aggregation.

40. A cardiac catheter apparatus comprising:
 a) a catheter body having proximal and distal end portions and a central lumen with a central longitudinal axis;
 b) the distal end portion of the body having a tip that extends laterally away from the central longitudinal axis of the lumen at the distal end portion of the catheter body;
 c) a support that extends radially from the catheter body to engage an aortic root, said support including a smoothly curved surface that gently engages the tissue of the aortic root during use;
 d) wherein the support is movable between extended and retracted positions; and
 e) a remote actuator that is manually grasped by a user at the distal end portion of the body for moving the support between extended and collapsed positions wherein the support extends longitudinally along the catheter body a distance that is greater than the support extends radially from the axis of the lumen.

41. A cardiac catheter apparatus comprising:
 a) a catheter body having proximal and distal end portions and a central lumen with a central longitudinal axis;
 b) the distal end portion of the body having a tip that extends laterally away from the central longitudinal axis of the lumen at the distal end portion of the catheter body;
 c) a support that extends radially from the catheter body to engage an aortic root, said support including a smoothly curved surface that gently engage the tissue of the aortic root during use;
 d) wherein the support is movable between extended and retracted positions;
 e) a remote actuator that is manually grasped by a user at the distal end portion of the body for moving the support between extended and retracted positions; and
 f) wherein the support is anchored to the catheter body distally at a pivotal connection.

42. A vascular catheter comprising:
 a) a catheter body comprising a single tube, having a proximal end, a distal end, at one inner lumen, and an outer surface; and
 b) one or more flexible support members attached to said catheter body at the distal end thereof, said support members being movable between a resting configuration positioned adjacent and generally parallel to said outer surface, and a support configuration wherein they are smoothly curved and extending away from said outer surface of said catheter, wherein the support members are covered with a hydrophilic surface material, preventing platelet adhesion and aggregation.

43. A vascular catheter comprising:
 a) a catheter body consisting of a single principal tube, having a proximal end, a distal end, at least one inner lumen, and an outer surface;
 b) one or more flexible support members attached to said outer surface of said catheter body at the distal end thereof, said support members being movable between a resting configuration position adjacent and generally parallel to said outer surface, and a support configuration wherein they are smoothly curved and extending away from said outer surface of said catheter; and c) said support members traversing parts or all of the outer wall of said catheter body at one or more points.

44. The vascular catheter of claim 43 wherein a plurality of support members are used, each of said support members is moved separately between the support configuration and the resting configuration.

45. The catheter as in claim 44 wherein the support members are comprised of flexible wires.

46. The catheter as in claim 45 wherein said wires run from the distal support section towards the proximal end of the catheter body through elongated tubular openings within the catheter wall.

47. The catheter as in claim 44 wherein said wires run from the distal support section towards the proximal end of the catheter adjacent to the outer surface of the catheter.

48. The catheter as in claim 44 wherein said wires run from the distal support section towards the proximal end of the catheter inside a lumen of the catheter.

49. The catheter as in claim 44, wherein a selected one of said wires assumes a variety of intermediate positions between the resting position and the extended position.

50. The catheter as in claim 44, wherein a plurality of said wires assumes a variety of intermediate positions between the resting position and the fully extended support position.

51. The catheter as in claim 50, wherein each of said wires is linked to a knob at the outer surface at the proximal end of said catheter, said wires being linked to said knobs by means of small connection pieces slidably positioned in longitudinal slots of said catheter wall.

52. The catheter as in claim 51, wherein the intersection between the outer surface of said catheter wall and the lower surface of said knobs is a cammed surface connection, said connection allowing to securely position said knobs at any intermediate position along the full length of said slots of said catheter wall.

53. The catheter as in claim 44, wherein the wires are firmly attached at their distal end near the tip of the catheter.

54. The catheter as in claim 44, wherein the wires are movably attached at their distal end by means of pivoting joints.

55. The catheter as in claim 44, wherein the inherent flexibility of the wires differs from said support section and the section between said support section and said knobs.

56. The catheter as in claim 44, wherein the inherent flexibility of the wires remains the same throughout the entire length from said support section to said knobs.

57. The catheter as in claim 44, wherein the inherent flexibility of the wires changes along the length of the support section.

58. The catheter of claim 44, wherein the inherent flexibility of the wires remains unchanged along the support section.

59. The catheter of claim 44, wherein all wires are of the same length.

60. The catheter of claim 44, wherein the wires used have different lengths.

61. The catheter of claim 44, wherein the wires used have different lengths, and more than one support sections are formed.

62. A vascular catheter comprising:

a) a catheter body consisting of a single principal tube, having a proximal end, a distal end, at least one inner lumen, and an outer surface;

b) one or more flexible support members attached to said outer surface of said catheter body at the distal end thereof, said support members being movable between a resting configuration position adjacent and generally parallel to said outer surface, and a support configuration wherein they are smoothly curved and extending away from said outer surface of said catheter; and c) said support members are to be locked in either a collapsed or an extended configuration.

63. The vascular catheter of claim 62 wherein a plurality of support members are used, each of said support members is moved separately between the support configuration and the resting configuration.

64. The catheter as in claim 62 wherein the support members are comprised of flexible wires.

65. The catheter as in claim 64 wherein said wires run from the distal support section towards the proximal end of the catheter body through elongated tubular openings within the catheter wall.

66. The catheter as in claim 62, wherein said wires run from the distal support section towards the proximal end of the catheter adjacent to the outer surface of the catheter.

67. The catheter as in claim 62, wherein said wires run from the distal support section towards the proximal end of the catheter inside the lumen of the catheter.

68. The catheter as in claim 62, wherein a selected one of said wires assumes a variety of intermediate positions between the resting position and the extended position.

69. The catheter as in claim 62, wherein a plurality of said wires assumes a variety of intermediate positions between the resting position and the fully extended support position.

70. The catheter as in claim 69, wherein each of said wires is linked to a knob at the outer surface at the proximal end of said catheter, said wires being linked to said knobs by means of small connection pieces slidably positioned in longitudinal slots of a catheter wall.

71. The catheter as in claim 70, wherein the intersection between the outer surface of the wall of said catheter and the lower surface of said knobs is a cammed surface connection, said connection allowing to securely position said knobs at any intermediate position along the full length of said slots of said wall of said catheter.

72. The catheter as in claim 62, wherein the wires are firmly attached at the distal end near the tip of the catheter.

73. The catheter as in claim 62, wherein the wires are movably attached at the distal end by means of pivoting joints.

74. The catheter as in claim 62, wherein the inherent flexibility of the wires differs from said support section and the section between said support section and said knobs.

75. The catheter as in claim 62, wherein the inherent flexibility of the wires remains the same throughout the entire length from said support section to said knobs.

76. The catheter as in claim 62, wherein the inherent flexibility of the wires changes along the length of the support section.

77. The catheter of claim 62, wherein the inherent flexibility of the wires remains unchanged along the support section.

78. The catheter of claim 62, wherein all wires are of the same length.

79. The catheter of claim 62, wherein the wires used have different lengths.

80. The catheter of claim 62, wherein the wires used have different lengths, and more than one support sections are formed.

81. A cardiac catheter apparatus comprising:
a) a catheter body having proximal and distal end portions and at least one inner lumen, and an outer surface;
b) a support that extends radially from the catheter body to engage an aortic root, said support forming a smoothly curved surface that gently engages the tissue of the aortic root during use;
c) wherein the support is movable between extended and retracted positions;
d) a remote actuator that is manually grasped by a user at the distal end portion of the catheter body for moving the support between extended and retracted positions; and
e) means for locking said support in at least one extended position during use.

82. The catheter apparatus of claim 81 wherein the support is comprised of a plurality of individual support members.

83. The catheter apparatus of claim 81 wherein the support is comprised of a plurality of individual wire members.

84. The catheter apparatus of claim 81 wherein the catheter body has a wall and the support is slidably mounted in the wall at least along a portion of the length of the catheter wall.

85. A method of using a catheter assembly for coronary angioplasty, wherein the catheter assembly comprises:
a guide catheter having a proximal end, a distal end, at least one inner lumen, an outer surface, and one or more flexible support members being movable between a resting configuration positioned adjacent and generally parallel to said outer surface, and at least one support configuration wherein they are extending away from said outer surface of said guide catheter, at least one of said one or more support members having means to be reversibly locked in at least one support configuration;
a catheter guide wire fitting into said at least one inner lumen of said guide catheter;
a dilating catheter having an inflatable balloon near its distal end;
a coronary guide wire positioned slidably within an inner lumen of said dilating catheter along at least part of the length of said catheter;
and wherein the method comprises the steps of:
a) placing said catheter guide wire into said at least one inner lumen of said guide catheter, such that a distal portion of said catheter guide wire exits said guide catheter at its distal tip;
b) inserting said guide catheter and said catheter guide wire into a percutaneously accessible artery of a patient;
c) advancing said guide catheter and said catheter guide wire through the arterial system until the tip of said guide catheter reaches the ascending aorta;
d) removing said catheter guide wire from said guide catheter;
e) maneuvering the proximal end of said guide catheter until its distal tip engages the ostium of a selected coronary artery;
f) maneuvering said at least one support members into a support configuration by bringing said at least one support members into contact with the endothelial surface of the ascending aorta, thereby minimizing the chance of disengagement of said tip of said guide catheter from the coronary ostium;
g) introducing said coronary guide wire and said dilating catheter into said at least one inner lumen of said guide catheter;
h) advancing said coronary guide wire into the coronary artery and through and beyond a coronary target lesion previously identified;
i) advancing said dilating catheter into the coronary artery until said dilating balloon reaches the previously identified target lesion;
j) inflating the balloon of said dilating catheter, thereby increasing the luminal diameter of the coronary artery at the site of the previously identified target lesion.

* * * * *